United States Patent [19]

Vorbrüggen

[11] 4,391,814
[45] Jul. 5, 1983

[54] DERIVATIVES OF ANTIPHLOGISTICALLY EFFECTIVE CARBOXYLIC ACIDS, THEIR PREPARATION AND MEDICINAL USE

[75] Inventor: Helmut Vorbrüggen, Berlin, Fed. Rep. of Germany

[73] Assignee: Schering Aktiengesellschaft, Berlin and Bergkamen, Fed. Rep. of Germany

[21] Appl. No.: 334,023

[22] Filed: Dec. 23, 1981

[30] Foreign Application Priority Data

Dec. 23, 1980 [DE] Fed. Rep. of Germany ....... 3049405

[51] Int. Cl.³ .................... A01N 43/76; A01N 43/80; A01N 43/54; A01N 43/50
[52] U.S. Cl. .................................. 424/272; 548/237; 548/238; 548/239; 548/146; 548/348; 548/355; 544/53; 544/55; 544/88; 544/96; 544/242; 546/275; 260/244.4; 260/245.1; 260/245.5; 260/245.6; 260/245.7; 260/330; 260/330.6; 424/251; 424/270; 424/273; 424/263
[58] Field of Search ...................... 548/237, 238, 239; 424/272

[56] References Cited

U.S. PATENT DOCUMENTS

| | | | |
|---|---|---|---|
| 3,726,893 | 4/1973 | Chen et al. | 548/237 |
| 3,901,906 | 8/1975 | Kozlik | 548/237 |
| 3,969,402 | 7/1976 | Adams et al. | 548/237 |

FOREIGN PATENT DOCUMENTS

| | | | |
|---|---|---|---|
| 3297 | 1/1979 | European Pat. Off. | 424/272 |
| 2830141 | 1/1980 | Fed. Rep. of Germany | 424/272 |
| 2010254 | 6/1979 | United Kingdom | 424/272 |

Primary Examiner—Donald G. Daus
Assistant Examiner—S. A. Gibson
Attorney, Agent, or Firm—Millen & White

[57] ABSTRACT

Compounds of Formula I

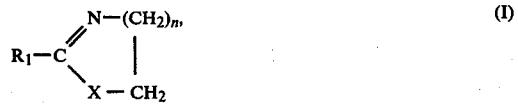

wherein
  $R_1$ is the residue of an antiphlogistically effective carboxylic acid of the formula $R_1COOH$,
  n is an integer 1, 2, or 3, and
  X is oxygen, sulfur, or optionally alkylated nitrogen
have valuable antiinflammatory activity.

8 Claims, No Drawings

DERIVATIVES OF ANTIPHLOGISTICALLY EFFECTIVE CARBOXYLIC ACIDS, THEIR PREPARATION AND MEDICINAL USE

The present invention relates to novel derivatives of antiphlogistically effective carboxylic acids, their preparation and medicinal use.

SUMMARY OF THE INVENTION

It is an object of this invention to provide such derivatives having advantages over the corresponding prior art compounds.

Upon further study of the specification and appended claims, further objects and advantages of this invention will become apparent to those skilled in the art.

These objects have been achieved by providing novel derivatives of antiphlogistically effective carboxylic acids,

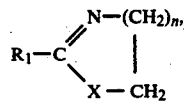
(I)

wherein
$R_1$ is the residue of an antiphlogistically effective carboxylic acid of the formula $R_1COOH$,
n is an integer 1, 2, or 3, and
X is oxygen, sulfur, or optionally alkylated nitrogen.

The novel derivatives of Formula I exhibit approximately the same antiphlogistic effectiveness as the corresponding carboxylic acids themselves, but they are distinguished in that they cause practically no gastric ulcers, as contrasted to the carboxylic acids.

DETAILED DESCRIPTION

Suitable antiphlogistically effective carboxylic acids $R_1COOH$ from which the novel derivatives of Formula I are derived include, for example, those of Formula IIa

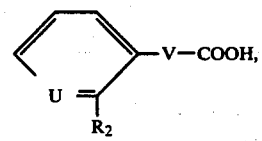
(IIa)

wherein
$R_2$ is (i) alkanoyl or alkanoyloxy each of 2–6 carbon atoms; or (ii) phenoxy, anilino or 1-naphthylamino each optionally substituted by halogen (especially chlorine or fluorine, but also Br and I), trifluoromethyl, or alkyl of 1–4 carbon atoms (especially methyl).
U is —CH= or —N=, and
V is a carbon-to-carbon bond or methylene.

Such carboxylic acids of Formula IIa include, for example:

2-acetoxybenzoic acid
2-[(2,6-dichlorophenyl)amino]phenylacetic acid
2-[(2,4-dichloro-1-naphthyl)amino]phenylacetic acid
2-[(2,4-dichlorophenyl)oxy]phenylacetic acid
2-[(2,3-dimethylphenyl)amino]benzoic acid
2-[(3-trifluoromethylphenyl)amino]benzoic acid
2-[(2,6-dichloro-3-methylphenyl)amino]benzoic acid
2-[(2-chloro-3-methylphenyl)amino]benzoic acid
2-[(3-chloro-2-methylphenyl)amino]benzoic acid
2-[(3-trifluoromethylphenyl)amino]-3-pyridinecarboxylic acid
2-[(2-methyl-3-trifluoromethylphenyl)amino]-3-pyridinecarboxylic acid or
2-[(3-chloro-2-methylphenyl)amino]-3-pyridinecarboxylic acid.

For such acids, see, for example T. J. Shen: Nonsteroidal Anti-inflammatory Agents in Burger's Medicinal Chemistry 4. Ed. 1981 Part III pages 1205–1272, whose disclosures are incorporated by reference herein.

Thus, the corresponding novel derivatives of this invention of these antiphlogistically active carboxylic acids of Formula IIa are of Formula Ia

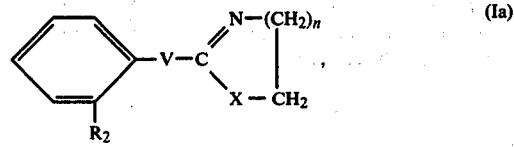
(Ia)

wherein n, $R_2$, U, V, and X are as defined above.

Other suitable antiphlogistically effective carboxylic acids $R_1COOH$ from which the novel derivatives of Formula I are derived furthermore include those of Formula IIb

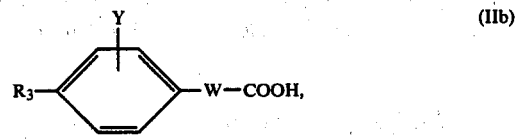
(IIb)

wherein
$R_3$ is straight-chain or branched alkyl or alkylene of 2–6 carbon atoms; cycloalkyl of 3–7 carbon atoms; cycloalkylalkyl of 4–8 carbon atoms; 2-oxocyclopentylidenemethyl; phenyl optionally substituted by halogen (preferably fluorine or chlorine but also Br or I), alkyl of 1–4 carbon atoms (preferably methyl) or trifluoromethyl; alkylamino of 1–6 carbon atoms; alkenyl or alkenylamino of 1–6 carbon atoms, 2,5-dihydropyroll-yl; 2,5-dihydropyran-1-yl; or 1-oxo-2-isoindolinyl;
Y is hydrogen or halogen (preferably fluorine or chlorine, but also Br or I), and
W is a carbon-to-carbon bond or an (optionally branched) alkylene or alkylidene group of 1–4 carbon atoms each optionally substituted by oxo, hydroxy, or halogen (F, Cl, Br, I) and/or interrupted by an oxygen atom or a sulfur atom or terminated at the phenyl (or correspondingly) attached end by oxy or thio.

Such carboxylic acids include, for example:
4-(4-biphenyl)-4-oxobutyric acid
4-(4-biphenyl)-4-hydroxybutyric acid
3-(2'-fluoro-4-biphenyl)butyric acid
4-(2'-fluoro-4-biphenyl)-4-oxobutyric acid
2[(4'-chloro-4-biphenyl)methyloxy]-2-methylpropionic acid
4-(4-biphenyl)-3-hydroxybutyric acid
2'-fluoro-4-biphenylacetic acid
2-(2'-fluoro-4-biphenyl)propionic acid 2-(2-fluoro-4-biphenyl)propionic acid
2-(2-methylpropyl)phenylpropionic acid
2-(4-isopropylphenyl)propionic acid
2-[4-(2-butenylamino)phenyl]propionic acid
2-[4-(1-oxoisoindolinyl)phenyl]butyric acid
2-[4-(1-oxoisoindolinyl)phenyl]propionic acid
2-[4-(2,5-dihydropyran-1-yl)phenyl]propionic acid
2-(4-cyclohexylphenyl)propionic acid
2-(3-chloro-4-cyclohexylphenyl)propionic acid
4-(3-chloro-4-cyclohexylphenyl)-4-oxobutyric acid
2-[4-(2-oxocyclopentylidene)methylphenyl]propionic acid or
4-(2-methylpropyl)phenylacetic acid.

For such acids, see, for example T. J. Shen: Nonsteroidal Anti-inflammatory Agents in Burger's Medicinal Chemistry 4. Ed. 1981 Part III pages 1205-1272, whose disclosures are incorporated by reference herein.

Thus, the novel derivatives of the antiphlogistically effective carboxylic acids of Formula IIb also include those of Formula Ib

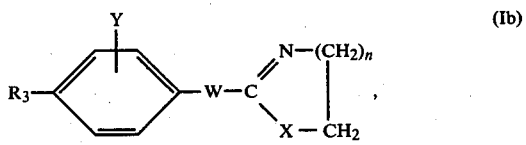

wherein n, R₃, X, Y, and W are as defined above.

Suitable antiphlogistically effective carboxylic acids R₁COOH from which the novel derivatives of Formula I are also derived include those of Formula IIc

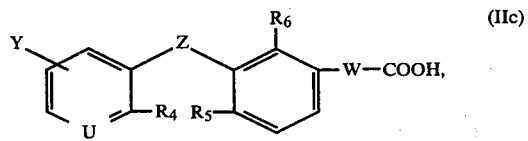

wherein
Y, U, and W are as defined above and Y can also be oxo,
Z is a carbon-to-carbon bond, methylene, carbonyl, oxygen, methyleneoxy (—CH₂—O—), methylenethio (—CH₂—S—), or methyleneamino (—CH₂—N—);
R₄ and R₅ each is hydrogen or jointly represent oxygen, sulfur, nitrogen, amino, carbonyl, methylene, or a carbon-to-carbon bond;
with the proviso that R₄ and R₅ are different from Z; and
R₆ is hydrogen or amino.
Such carboxylic acids of Formula IIc include, for example:

2-(3-benzoylphenyl)propionic acid
2-(3-phenoxyphenyl)propionic acid
2-(2fluorenyl)propionic acid
2-(6-chloro-2-carbazolyl)propionic acid
2-(6-oxo-3-xanthenyl)propionic acid
10-methyl-2-phenothiazinylacetic acid
2-(9-aza-3-xanthenyl)propionic acid
4-(3-diphenyloxidyl)-4-oxobutyric acid
2-(3-phenoxy-2-aminophenyl)propionic acid
(11-oxo-6,11-dihydrodibenz[b,e]oxepin-3-yl)acetic acid or (11-oxo-6,11-dihydrodibenz[b,e]thiepin-3-yl)acetic acid.

For such acids, see, for example T. J. Shen: Nonsteroidal Anti-inflammatory Agents in Burger's Medicinal Chemistry 4. Ed. 1981 Part III pages 1205-1272, whose disclosures are incorporated by reference herein.

The corresponding novel derivatives of this invention of these antiphlogistically effective carboxylic acids of Formula IIc are characterized by Formula Ic

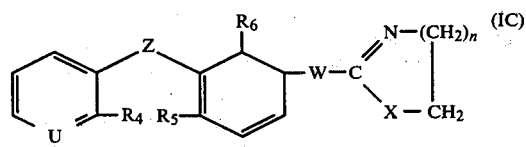

wherein n, X, Z, U, W, R₄, R₅, and R₆ are as defined above.

Further suitable antiphlogistically active carboxylic acids R₁COOH from which the novel derivatives of Formula I are derived also include those of Formula IId

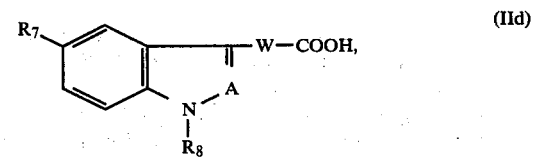

wherein
W is as defined above,
A is nitrogen or CH₃C—,
R₇ is hydrogen, halogen (F, Cl, Br, I), or methoxy, and
R₈ is benzyl, benzoyl, or cinnamoyl, each optionally substituted (preferably in the para-position) by halogen (preferably chlorine, but also F, Br or I), azido, methylthio, or methylsulfynyl.

Such carboxylic acids include, for example:

(1-benzyl-1H-indazol-3-yloxy)acetic acid
1-(4-chlorobenzoyl)-5-methoxy-2-methyl-3-indolylacetic acid
2-[1-(4-methylthiobenzyl)-5-methoxy-2-methyl-3-indolyl]propionic acid
1-(4-azidobenzoyl)-5-methoxy-2-methyl-3-indolylacetic acid
1-(4-chlorobenzoyl)-5-methoxy-2-methyl-3-indolylacetoxyacetic acid or
1-cinnamoyl-5-methoxy-2-methyl-3-indolylacetic acid.

For such acids, see, for example T. J. Shen: Nonsteroidal Anti-inflammatory Agents in burger's Medicinal Chemistry 4. Ed. 1981 Part III pages 1205-1272, whose disclosures are incorporated by reference herein.

The corresponding novel derivatives of this invention of these antiphlogistically active carboxylic acids of Formula IId are of the Formula Id

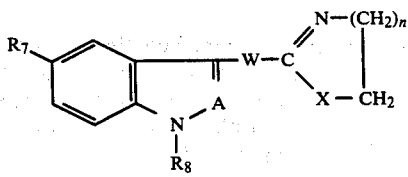

wherein n, A, X, W, R7, and R8 are as defined above.

Suitable antiphlogistically effective carboxylic acids R1COOH from which the novel derivatives of Formula I are derived furthermore include those of Formula IIe

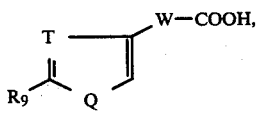

wherein
W is as defined above,
Q is oxygen, sulfur, or methylimino,
T is

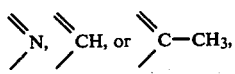

and
R9 is phenyl or benzoyl each optionally substituted by para-positioned chlorine or para-positioned methyl.

Such carboxylic acids include, for example:

5-(4-methylbenzoyl)-1-methylpyrrol-3-acetic acid
5-(4-chlorobenzoyl)-1,4-dimethylpyrrol-3-acetic acid or
3-[5-(4-chlorophenyl)furan-3-yl]-3-hydroxypropionic acid.

For such acids, see, for example T. J. Shen: Nonsteroidal Anti-inflammatory Agents in Burger's Medicinal Chemistry 4. Ed. 1981 Part III pages 1205-1272, whose disclosures are incorporated by reference herein.

The corresponding novel derivatives of this invention of these antiphlogistically active carboxylic acids of Formula IIe are of the Formula Ie

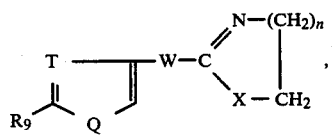

wherein n, Q, T, X, W, and R9 are as defined above.

Suitable antiphlogistically effective carboxylic acids R1COOH from which the novel derivatives of Formula I are derived also include those of formula IIf

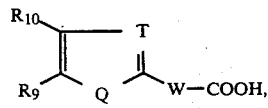

wherein

W, Q, T, and R9 are as defined above and
R10 is hydrogen, methyl, or phenyl or benzoyl, each optionally substituted by chlorine.

Such carboxylic acids, include, for example:

1-methyl-5-(4-methylbenzoyl)pyrrol-2-acetic acid
5-(4-chlorobenzoyl)-1,4-dimethylpyrrol-2-acetic acid
2-(5-benzoyl-2-thienyl)propionic acid
3-(4,5-dibenzoyl-2-oxazolyl)propionic acid or
4,5-di(4-chlorobenzoyl)-2-oxazolyl-thio-acetic acid.

For such acids, see, for example T. J. Shen: Nonsteroidal Anti-inflammatory Agents in Burger's Medicinal Chemistry 4. Ed. 1981 Part III pages 1205-1272, whose disclosures are incorporated by reference herein.

The corresponding novel derivatives of this invention of the Formula IIf are of the Formula If

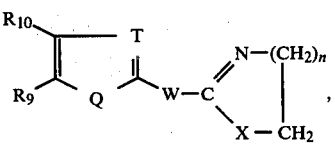

wherein n, X, Q, T, W, R9, and R10 are as defined above.

Further suitable antiphlogistically effective carboxylic acids, from which the novel derivatives of Formula I are derived, include those of Formula IIg

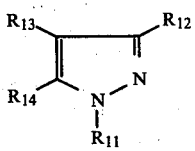

wherein
R11 is alkyl of up to 6 carbon atoms or phenyl optionally substituted by chlorine or fluorine, and
one of R12, R13, and R14 is an acetic acid residue; one or two of R12, R13, and R14 is phenyl optionally substituted by chlorine or fluorine; and, optionally, one of R12, R13, and R14 is hydrogen.

Such carboxylic acids include, for example:

4-(4-chlorophenyl)-1-(4-fluorophenyl)-3-pyrazolylacetic acid
1,3,5-triphenyl-4-pyrazolylacetic acid
1,3,4-triphenyl-5-pyrazolylacetic acid
3-(4-chlorophenyl)-1-phenyl-4-pyrazolylacetic acid or
1-(2-methylpropyl)-3,4-diphenyl-5-pyrazolylacetic acid.

For such acids, see, for example T. J. Shen: Nonsteroidal Anti-inflammatory Agents in Burger's Medicinal Chemistry 4. Ed. 1981 Part III pages 1205-1272, whose disclosures are incorporated by reference herein.

The following are further suitable antiphlogistically active carboxylic acids R1COOH from which the derivatives of Formula I can be derived, i.e., the following are equivalents of the foregoing mentioned R1COOH acids as are the corresponding derivatives of this invention equivalents of the aforementioned derivatives.

3-phenylbenzofuran-7-ylacetic acid
1-(4-chlorophenyl)-2,5-dimethylpyrrol-3-acetic acid
4-benzoylindan-1-carboxylic acid 6-chloro-5-cyclohexylindan-1-carboxylic acid
1-acetoxy-6-chloro-5-cyclohexylindan-1-carboxylic acid
2-isopropylindan-5-carboxylic acid
4-(2-methylpropyl)phenylacetic acid
2-[4-(2-methylpropyl)phenyl]propionic acid
6-chloro-5-cyclopentylmethylindan-1-carboxylic acid
2-[3-chloro-4-thenyl)phenyl]propionic acid
2-[4-(2-thenoyl)phenyl]propionic acid
1-chlorophenyl-2,4-dimethylpyrrol-3-acetic acid
4-(4-chlorophenyl)-2-phenyl-5-thiazolylacetic acid
2-(6-methoxy-2-naphthyl)propionic acid
2-[2-(4-chlorophenyl)benzoxazol-5-yl]propionic acid
4-chloro-3-propenyloxyphenylacetic acid
2-hydroxy-5-(pyrrol-1-yl)benzoic acid
2-hydroxy-5-(2,4-difluorophenyl)benzoic acid
5-fluoro-2-methyl-1-(4-methylsulfynylbenzylidene)indene-3-carboxylic acid
2-hydroxy-5-[2-phenyl(benz[f]indol-1-yl)]benzoic acid
3-(1-butyldihydropyrano[3,4-b]indol-1-yl)propionic acid
3-(1,5-diethyldihydropyrano[3,4-b]indol-1-yl)propionic acid or
3-(1-ethyldihydropyrano[3,4-b]indol-1-yl)propionic acid.

For such acids, see, for example T. J. Shen: Nonsteroidal Anti-inflammatory Agents in Burger's Medicinal Chemistry 4. Ed. 1981 Part III pages 1205–1272, whose disclosures are incorporated by reference herein.

Further equivalent $R_1$ groups are derived from other conventional antiphlogistic acids such as those of similar or equivalent structure.

In Formula (I), when X is optionally akylated nitrogen, the alkyl group is of 1–4 carbon atoms.

The novel derivatives of Formula I can be prepared conventionally according to a process comprising
(a) condensing a carboxylic acid or a derivative thereof, of Formula III

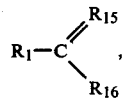 (III)

wherein
$R_1$ is as defined above,
$R_{15}$ is oxygen, sulfur, or alkylimino of 1–4 carbon atoms in the alkyl residue, and
$R_{16}$ is hydroxy, alkoxy of 1–6 carbon atoms, benzyloxy, trimethylsilyloxy, triethylsilyloxy, or tribenzyloxy with an amine of Formula IV

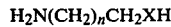 (IV), wherein n and X are as defined above; or
(b) cyclizing a compound of Formula V

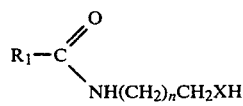 (V)

wherein $R_1$, n, and X are as defined above.

These processes can be conducted under conventional conditions. See, e.g., Angew, Ch. [Applied Chemistry] 88:321 [1976]; R. M. Acheson: An Introduction to the Chemistry of Heterocyclic Compounds: Interscience Publishers, New York [1967]: especially 308 and 322. These disclosures are incorporated by reference herein.

According to a preferred method, the compounds of Formula III (especially the carboxylic acids themselves) are reacted, in an inert solvent in the presence of a tertiary amine and a triphenylphosphine or trialkyl phosphine, with the amine of Formula IV. The compounds of Formula V are thus formed intermediarily, and during the further course of the reaction these are cyclized to the compounds of Formula I.

Suitable inert solvents include, for example, ethers (such as diethyl ether, diisopropyl ether, dioxane, or tetrahydrofuran), dipolar aprotic solvents (such as acetonitrile, dimethylformamide, hexamethylphosphoric triamide, dimethyl sulfoxide, or sulfolane), aromatic hydrocarbons (such as benzene, toluene, or xylene), chlorinated hydrocarbons (tetrachloromethane, chloroform, dichloromethane, tetrachloroethane), and mixtures of the aforementioned solvents, especially acetonitrile and pyridine.

Suitable tertiary amines include preferably trialkylamines, e.g. triethylamine, or N-heterocycles, such as pyridine, lutidine, or collidine, 2-dimethylaminopyridine, 4-dimethylaminopyridine, 1,5-diazabicyclo[4,3,0]non-5-ene, 1,8-diazabicyclo[5,4,0]undec-7-ene, or 1,4-diazabicyclo[2,2,2]octane.

The reaction is conducted in the presence of trialkyl phosphines (trimethylphosphine, triethylphosphine, etc.) or preferably in the presence of triphenylphosphine.

The starting materials necessary for these preparation reactions are all known or are preparable from compounds which are known using fully conventional procedures.

The compounds of this invention possess good antiinflammatory activity and are superior as compared with the corresponding antiinflammatorily active carboxylic acids per se in that they are practically free of ulcerogenic side effects when administered, e.g., to mammals, including humans.

Consequently, the novel compounds are suitable, in combination with the vehicles customary in galenic pharmacy, for the treatment of, for example, diseases of the rheumatic spectrum (such as ostearthritis or ankylosing spondylitis), bronchial asthma, hay fever, and others.

It is further noteworthy that the imidazole derivatives of Formula I are also suitable for treating migraine and dysmenorrhea, and reduce the risk of thrombosis.

The medicinal preparations of this invention are produced as usual by converting the active agents with suitable additives, carrier compounds, and flavorameliorating agents, etc., into the desired forms of administration, such as tablets, dragees, capsules, solutions, inhalants, etc.

Especially suitable for oral administration are tablets, dragees, and capsules, which contain, for example, 1–250 mg of the active ingredient and 50 mg to 2 g of a pharmacologically inactive carrier, such as, for example, lactose, amylose, talc, gelatin, magnesium stearate, and similar materials, as well as the usual additives.

Generally, the compounds of this invention are administered in dosages of 5–200 mg/day. They can be administered analogously to the corresponding carboxylic acids mentioned above.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings etc.

Dosages for a given host can be determined using conventional considerations, e.g., by customary comparison of the differential activities of the subject compound and of a known agent, by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

1.237 g of 2-(4-isobutylphenyl)propionic acid was dissolved in 50 ml of acetonitrile, combined with 0.366 g of ethanolamine, 2.53 g of triethylamine, and 3.176 g of carbon tetrachloride and then heated to 22°–26° C. Then a solution of 4.72 g of triphenylphosphine in 70 ml of absolute acetonitrile was added dropwise to the solution within three and a half hours; the reaction mixture was allowed to stand for 16 hours at room temperature and concentrated to dryness under vacuum at a bath temperature of 30° C.

The residue was combined with 100 ml of ethyl ether and 70 ml of 2 N aqueous sodium hydroxide solution, agitated for 30 minutes, and the organic phase was separated. The aqueous phase was additionally extracted three times with respectively 40 ml of ethyl ether; the combined ether phases were washed with 100 ml of saturated aqueous NaCl solution, dried over sodium sulfate, and evaporated to dryness under vacuum.

The resultant residue was combined with 100 ml of ethyl ether, based on a water bath, cooled to room temperature, and filtered. The filtrate was concentrated and chromatographed over a column of 80 g of silica gel with 40% water (Merck) by means of toluene-ethyl acetate 9:1, thus obtaining 1.18 g of 2-[1-(4-isobutylphenyl)ethyl]-2-oxazoline as a colorless oil.

$C_{15}H_{21}NO$     MW: 231.3

Calculated: C, 77.88; H, 9.15; N, 6.05. Found: C, 77.87; H, 9.50; N, 6.02.

EXAMPLE 2

1.382 g of 2-(6-methoxy-2-naphthyl)propionic acid (Naproxen) was dissolved in 50 ml of acetonitrile, combined with 0.366 g of ethanolaine, 2.53 g of triethylamine, and 3.176 g of carbon tetrachloride and then heated to 22°–26° C. Thereupon a solution of 4.72 g of triphenylphosphine in 70 ml of absolute acetonitrile was added dropwise to the solution within four hours; the reaction mixture was allowed to stand at room temperature for 3 days and concentrated to dryness under vacuum at a bath temperature of 30° C.

The residue was combined with 100 ml of ethyl ether and 70 ml of 2 N aqueous sodium hydroxide solution, stirred for 30 minutes, and the organic phase was separated. The aqueous phase was additionally extracted three times with respectively 40 ml of ethyl ether; the combined ether phases were washed with 100 ml of saturated aqueous sodium chloride solution, dried over sodium sulfate, and concentrated to dryness under vacuum.

The resultant residue was mixed with 100 ml of ethyl ether, heated on a water bath, cooled to room temperature, and filtered. The filtrate was concentrated, chromatographed with toluene over a column of 125 g of silica gel (Merck), and the yield was 1.01 g of 2-[1-(6-methoxy-2-naphthyl)ethyl]-2-oxazoline, mp 94°–96° C.

$C_{16}H_{17}NO_2$     MW: 255.3

Calculated: C, 75.27; H, 6.71; N, 5.49. Found: C, 74.87; H, 6.68; N, 5.57.

EXAMPLE 3

1.15 g of 2-(6-methoxy-2-naphthyl)propionic acid was dissolved in 50 ml of acetonitrile, combined with 0.375 g of 8-amino-1-propanol, 2.02 g of triethylamine, and 3.176 g of carbon tetrachloride, and then heated to 22°–26° C. Then a solution of 3.93 g of triphenylphosphine in 70 ml of absolute acetonitrile was added dropwise to the solution within three and a half hours; the reaction mixture was allowed to stand at room temperature for 72 hours and then concentrated under vacuum at 30° C. bath temperature to dryness.

The residue was combined with 150 ml of ethyl ether and 50 ml of 2 N aqueous sodium hydroxide solution, stirred for 30 minutes, and the organic phase was separated. The aqueous phase was additionally extracted three times with respectively 40 ml of ethyl ether; the combined ether phases were washed with 100 ml of saturated aqueous sodium chloride solution, dried over sodium sulfate, and evaporated to dryness under vacuum.

The thus-obtained residue was combined with 50 ml of ethyl ether, heated on a water bath, cooled to room temperature, and filtered. The filtrate was concentrated, chromatographed with toluene over a column of alkaline aluminum oxide, activity stage IV (Woelm), and the product was 0.745 g of 2-[1-(6-methoxy-2-naphthyl)ethyl]-2-(5,6-dihydro-4H-1,3-oxazine), mp 113°–115° C.

$C_{17}H_{19}NO_2$   MW: 264.3

Calculated: C, 75.81; H, 7.11; N, 5.2. Found: C, 75.84; H, 7.47; N, 4.92.

EXAMPLE 4

1.984 g of 4-(4-chlorophenyl)-1-(4-fluorophenyl)-3-pyrazolacetic acid was dissolved in 100 ml of acetonitrile, combined with 0.366 g of ethanolamine, 3.04 g of triethylamine, and 3.176 g of carbon tetrachloride, and then heated to 22°–26° C. Thereafter a solution of 4.72 g of triphenylphosphine in 70 ml of absolute acetonitrile was added dropwise to the solution within three and a half hours; the reaction mixture was allowed to stand for three days at room temperature and then evaporated to dryness under vacuum at a bath temperature of 30° C.

The residue was combined with 100 ml of ethyl ether and 70 ml of 2 N aqueous sodium hydroxide solution, stirred for 30 minutes, and the organic phase was separated. The aqueous phase was additionally extracted three times with respectively 40 ml of ethyl ether, the combined ether phases were washed with 100 ml of saturated sodium chloride solution, dried over sodium sulfate, and concentrated to dryness under vacuum.

The thus-produced residue was combined with 100 ml of ethyl ether, heated on a water bath, cooled to room temperature, and filtered. The filtrate was concentrated, chromatographed with toluene over a solumn of 80 g of silica gel (Merck), and the yield was, after recrystallization from cyclohexane, 0.65 g of 2-{[4-(4-chlorophenyl)-1-(4-fluorophenyl)-3-pyrazolyl]methyl}-2-oxazoline.

$C_{19}H_{15}ClFN_3O$   MW: 355.81

Calculated: C, 64.14; H, 4.25; N, 11.81. Found: C, 64.56; H, 4.63; N, 11.45.

EXAMPLE 5

1.59 g of sodium 2-[2,6-dichlorophenyl)amino]phenylacetate was dissolved in 70 ml of acetonitrile, combined with 0.305 g of ethanolamine, 2.02 g of triethylamine, and 3.176 g of carbon tetrachloride, and then heated to 22°–26° C. Within three and a half hours, a solution of 3.93 g of triphenylphosphine in 80 ml of absolute acetonitrile was then added dropwise to the solution; the reaction mixture was allowed to stand at room temperature for 22 hours and then concentrated to dryness under vacuum at a bath temperature of 30° C.

The residue was combined with 200 ml of toluene and 100 ml of 2 N aqueous sodium hydroxide solution, stirred for 30 minutes, and the organic phase was separated. The aqueous phase was additionally extracted three times with respectively 100 ml of toluene, the combined toluene phases were dried over sodium sulfate and concentrated to dryness under vacuum.

The resultant residue was chromatographed with toluene over a column of 200 g of aluminum oxide, activity stage IV (Woelm), thus obtaining after recrystallization from ethanol, 0.655 g of 2-[2-(2,6-dichloroanilino)benzyl]-2-oxazoline, mp 141° C.

$C_{16}H_{14}N_2OCl_2$   MW: 321.22

Calculated: C, 59.83; H, 4.39; N, 8.72; Cl, 22.08. Found: C, 59.68; H, 4.56; N, 8.44; Cl, 21.54.

EXAMPLE 6

1.406 g of 2-[(3-trifluoromethylphenyl)amino]benzoic acid was dissolved in 60 ml of acetontrile, combined with 0.305 g of ethanolamine, 2.02 g of triethylamine, and 3.176 g of carbon tetrachloride, and then heated to 22°–26° C. Then a solution of 3.43 g of triphenylphosphine in 80 ml of absolute acetonitrile was added dropwise to the solution within three and a half hours; the reaction mixture was allowed to stand for 20 hours at room temperature, and then concentrated to dryness under vacuum at a bath temperature of 30° C.

The residue was combined with 150 ml of ethyl ether and 40 ml of 2 N aqueous sodium hydroxide solution, stirred for 30 minutes, and the organic phase was separated. The aqueous phase was additionally extracted three times with respectively 40 ml of ethyl ether; the combined ether phases were washed with 100 ml of saturated aqueous sodium chloride solution, dried over sodium sulfate, and evaporated to dryness under vacuum.

The resultant residue was combined with 100 ml of ethyl ether, heated on a water bath, cooled to room temperature, and filtered. The filtrate was concentrated, chromatographed with toluene over a column of 120 g of alkaline aluminum oxide, activity stage IV (Woelm), and the product was 1.02 g of 2-(3'-trifluoromethylanilino)phenyl-2-oxazoline as a colorless oil.

$C_{16}H_{13}N_2OF_3$   MW: 306.28

Calculated: C, 62.74; H, 4.28; N, 9.15; F, 18.61. Found: C, 63.02; H, 4.49; N, 8.93; F, 18.69.

EXAMPLE 7

A solution of 3.93 g of triphenylphosphine in 80 ml of absolute acetonitrile was added dropwise under stirring at 25° C. under argon to a solution of 1.789 g of 1-p-chlorobenzoyl-2-methyl-5-methoxyindol-3-acetic acid, 0.305 g of ethanolamine, 2.02 g of triethylamine, and 3.176 g of carbon tetrachloride in 100 ml of absolute acetonitrile, for a period of three and a half hours. After 18 hours at 24° C., the mixture was evaporated under vacuum and the crystalline residue agitated with 200 ml of ethyl ether and 75 ml of 2 N aqueous sodium hydroxide solution. After separation of the aqueous phase and secondary extraction with three times 40 ml of ethyl ether, the combined ether extracts were dried ($Na_2SO_4$) and concentrated, during which step triphenylphosphine oxide was crystallized. The filtrate was evaporated and chromatographed with toluene on 210 g of aluminum oxide, activity stage IV (alkaline; Woelm); after a forerun of 300 ml, the subsequent 800 ml of eluate yielded 1.38g of a light-yellow, oily (4-chlorophenyl)-[5-methoxy-2-methyl-3-(oxazolin-2-ylmethyl)-1-indolyl]ketone.

$C_{21}H_{19}N_2O_3Cl$

Calculated: C, 65.88; H, 5.00; N, 7.32. Found: C, 65.51; H, 4.82; N, 7.45.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula

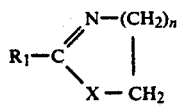

wherein
n is 1;
X is oxygen; and
$R_1$ is of the formula:

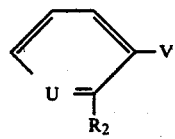 (a)

wherein
$R_2$ is (i) alkanoyl or alkanoyloxy each of 2–6 carbon atoms; (ii) phenoxy, anilino or 1-naphthylamino; or (iii) phenoxy, anilino or 1-naphthylamino, each of which is mono- or di-substituted by halogen, trifluoromethyl, or alkyl of 1–4 carbon atoms;
U is —CH= and
V is a carbon-to-carbon bond or methylene;
or

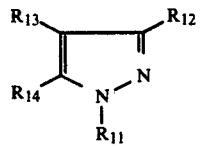 (b)

wherein
$R_{11}$ is alkyl of up to 6 carbon atoms, phenyl or phenyl mono- or di-substituted by chlorine or fluorine;
one of $R_{12}$, $R_{13}$, and $R_{14}$ is methylenyl; one or two of $R_{12}$, $R_{13}$, and $R_{14}$ is phenyl or phenyl mono- or di-substituted by chlorine or fluorine; or one of $R_{12}$, $R_{13}$, and $R_{14}$ is hydrogen.

2. 2-[1-(6-Methoxy-2-naphthyl)ethyl]-2-oxazoline.
3. 2-([4-(4-Chlorophenyl)-1-(4-fluorophenyl)-3-pyrazolyl]methyl)-2-oxazoline, a compound of claim 1.
4. 2-[2-(2,6-Dichloroanilino)benzyl]-2-oxazoline, a compound of claim 1.
5. 2-(3-Trifluoromethylanilino)phenyl-2-oxazoline, a compound of claim 1.
6. A pharmaceutical composition comprising an antiinflammatorily effective amount of a compound of claim 1 and a pharmaceutically acceptable carrier.
7. A pharmaceutical composition of claim 6 wherein the amount of antiinflammatory compound is 1–250 mg.
8. A method of treating inflammation in a patient comprising administering to the patient an antiinflammatorily effective amount of a compound of claim 1.

* * * * *